US006936262B2

(12) United States Patent
Briggs et al.

(10) Patent No.: US 6,936,262 B2
(45) Date of Patent: *Aug. 30, 2005

(54) LKTA DELETION MUTANT OF P. HAEMOLYTICA

(75) Inventors: Robert E. Briggs, Boone, IA (US); Fred M. Tatum, Ames, IA (US)

(73) Assignee: Biotechnology Research and Development Corporation, Peoria, IL (US)

( * ) Notice: Subject to any disclaimer, the term of this patent is extended or adjusted under 35 U.S.C. 154(b) by 2 days.

This patent is subject to a terminal disclaimer.

(21) Appl. No.: 10/055,174

(22) Filed: Jan. 25, 2002

(65) Prior Publication Data

US 2002/0150584 A1 Oct. 17, 2002

Related U.S. Application Data

(60) Division of application No. 09/245,331, filed on Feb. 5, 1999, now abandoned, which is a continuation-in-part of application No. 09/160,340, filed on Sep. 25, 1998, now Pat. No. 6,331,303.
(60) Provisional application No. 60/060,060, filed on Sep. 25, 1997.

(51) Int. Cl.$^7$ .............................................. A61K 39/02
(52) U.S. Cl. ............................... 424/255.1; 424/234.1; 424/172.1; 424/252.3; 424/439; 424/442; 424/193.1; 435/69.1; 435/320.1; 530/350
(58) Field of Search .......................... 424/255.1, 234.1, 424/172.1, 252.3, 439, 422, 193.1; 435/69.1, 320.1; 530/350

(56) References Cited

U.S. PATENT DOCUMENTS

| 5,422,110 A | 6/1995 | Potter et al. |
|---|---|---|
| 5,476,657 A | 12/1995 | Potter |
| 5,733,780 A | 3/1998 | Briggs et al. |

FOREIGN PATENT DOCUMENTS

| WO | WO 97 16531 A1 | 5/1997 |
|---|---|---|
| WO | 97/41823 A | 11/1997 |

OTHER PUBLICATIONS

George L. Murphy et al. "Hemolytic Activity of the *Pasteurella haemolytica* Leukotoxin" Infection and Immunity, Aug. 1995, pp. 3209–3212.

Natalie D. Fedorova & Sarah K. Highlander "Generation of Targeted Nonpolar Gene Insertions and Operon Fusions in *Pasteurella haemolytica* and Creation of a Strain that Produces and Secretes Inactive Leukotoxin" Infection and Immunity, Jul. 1997, pp. 2593–2598.

Fred M. Tatum et al. "Construction of an isogenic leukotoxin deletion mutant of *Pasteurella* haemolytica serotype 1: characterization and virulence" Microbial Pathagenesis 1998; 24:37–46.

Robert E. Briggs et al. "Development and testing of a unique strain of *Pasteurella* haemolytica for use in studies on colonization of the respitory tract of cattle" AJVR, vol. 59, No. 4, Apr. 1998.

Robert E. Briggs et al. "Rapid spread of a unique strain of *Pasteurella haemolytica* serotype 1 among transported calves" AJVR, vol. 59, No. 4, Apr. 1998.

Glynn H. Frank et al. "Colonization of the tonsils and nasopharynx of calves by a rifampicin–resistant *Pasteurella haemolytica* and its inhibition by vaccination" Am J Vet Res., vol. 56, No. 7, Jul. 1995.

G.H. Frank et al. "Serotype–specific inhibition of colonization of the tonsils and nasopharynx of calves after *Pasteurella haemolytica* serotype A1 after vaccination with the organism" Am J Vet Res, vol. 55, No. 8, Aug. 1994.

G.H. Frank & R.E. Briggs "Colonization of the tonsils of calves with *Pasteurella haemolytica*" Am J Vet Res, vol. 53, No. 4, Apr. 1992.

Glynn H. Frank "Infection of the middle nasal meatus of calves with *Pasteurella haemolytica* serotype 1" Am J Vet Res, vol. 50, No. 8, Aug. 1989.

David C. Straus et al. "In Vivo Production of Neuraminidase by *Pasteurella haemolytica* in Market Stressed Cattle After Natural Infection" Current Microbiology, vol. 37 (1998) pp. 240–244.

Glynn H. Frank et al. "Respiratory tract disease and mucosal colonization by *Pasteurella haemolytica* in transported cattle" AJVR, vol. 57, No. 9, Sep. 1996 pp. 1317–1320.

Cruz W.T. et al. "Deletion analysis resolves cell–binding and lytic domains of the Pasteurelle leutoxn" Molecular Microbiology, vol. 4, No. 11, Nov. 1990, pp. 1933–1939.

Petras S.F. et al. "Antigenic and virulence properties of Pasteurella haemolytica leukotoxin mutants" Infection and Immunity, vol. 63, No. 5, Mar. 1995, pp. 1033–1039.

Homchampa et al. "Cross protective immunity conferred by a marker–free *aro A* mutant of *Pasteurella multocida*" Vaccine 1997, vol. 15, No. 2.

Beaumont et al. "Identification and characterization of *al R*, a Gene Encoding an AraC–Like Regulator of Alcaligin Siderophore Biosynthesis and Transport in *Bordetella ppertussis* and *Bordetella bronchiseptica*" Journal of Bacteriology, Feb. 1998, pp. 862–870, vol. 180, No. 4.

Link et al. "Methods for Generating Precise Deltions and Insertions in the Genome of Wild–Type *Escherichia coli:* Application to Open Reading Frame Characterization" Journal of Bacteriology, Oct. 1997, pp. 628–6237, vol. 179, No. 20.

(Continued)

*Primary Examiner*—Jennifer E. Graser
(74) *Attorney, Agent, or Firm*—Banner & Witcoff, Ltd.

(57) ABSTRACT

Mutants of *P. haemolytica* provide excellent safety and efficacy when used as vaccines in ruminants, for example cattle, sheep, and goats, subject to pneumonic pasteurellosis. They can be administered by a variety of routes. Especially preferred is the use in animal feeds. The mutants are not reverting and contain no foreign DNA and no introduced antibiotic resistance genes.

24 Claims, 6 Drawing Sheets

OTHER PUBLICATIONS

Cotter and Miller "BvgAS–Medicated Signal Transduction: Analysis of Phase–Locked Regulatory Mutants of *Bordetella bronchiseptica* in a Rabbit Model" Infection and Immunity Aug. 1994, pp. 3381–3390, vol. 62, No. 8.

Hamilton et al. "New Method for Generating Deletions and Gene Replacements in *Escherichia coli"* Journal of Bacteriology, Sep. 1989, pp. 4617–4622, vol. 171, No. 9.

Murphy G.L. et al. "Haemolytic activity of the Pasteurella haemolytica leukotoxin" Infection and Immunity, vol. 63, No. 8, Aug. 1995, pp. 3209–3212.

Cruz W.T. et al. "Deletion analysis resolves cell–binding and lytic domains of the Pasteurella leukotoxin" Molecular Microbiology, vol. 4, No. 11, Nov. 1990, pp. 1933–1939.

Petras S.F. et al. "Antigenic and virulence properties of Pasteurella haemolytica leukotoxin mutants" Infection and Immunity, vol. 63, No. 5, Mar. 1995, pp. 1033–1039.

Boslego et al., "Gonorrhea Vaccines", Vaccines and Immunotherapy, 1991, pp. 211–233, Chapter 17.

SEQUENCE LISTING

<160> NUMBER OF SEQ ID NOS: 2

<210> SEQ ID NO 1
<211> LENGTH: 26
<212> TYPE: DNA
<213> ORGANISM: Pasteurella cf. haemolytica

<400> SEQUENCE: 1
ccggatcccc aattcgtaga ggtttc         26

<210> SEQ ID NO 2
<211> LENGTH: 26
<212> TYPE: DNA
<213> ORGANISM: Pasteurella cf. haemolytica

<400> SEQUENCE: 2
ccggatccgc tgaaagcggt cggggg         26

LKTA DELETION MUTANT OF *P. HAEMOLYTICA*

This application is a division of Ser. No. 09/245,331 filed Feb. 5, 1999, abandoned, which is a continuation in part of Ser. No. 09/160,340 filed Sep. 25, 1998, now U.S. Pat. No. 6,331,303, which claim the benefit of co-pending provisional application Ser. No. 60/060,060, filed Sep. 25, 1997. Each of these applications is incorporated by reference herein.

TECHNICAL FIELD OF THE INVENTION

This invention is related to the field of bacterial genetics and more particularly to the field of respiratory pathogens of farm animals.

BACKGROUND OF THE INVENTION

*P. haemolytica* as a pathogen causes serious economic damage to the animal farming industry. Vaccines which have been developed in an effort to control the disease have met with variable but limited success. Because the disease is caused in significant part by the animals' own reaction to *P. haemolytica* infection, inappropriately designed vaccines may actually worsen the clinical condition of infected vaccinates. Thus, there is a continuing need in the art for safe and effective vaccines which can reduce the morbidity and/or mortality of ruminants due to *P. haemolytica*.

SUMMARY OF THE INVENTION

It is an object of the present invention to provide a *P. haemolytica* bacterium useful as a vaccine strain.

It is another object of the present invention to provide a method of inducing immunity to pneumonic pasteurellosis in ruminants.

It is an object of the present invention to provide a vaccine strain against pneumonic pasteurellosis.

Another object of the invention is to provide a ruminant feed.

Another object of the invention is to provide a temperature sensitive plasmid for manipulation of *P. haemolytica*.

These and other objects of the invention are achieved by one or more of the embodiments described below. One embodiment of the invention provides a *P. haemolytica* bacterium which expresses no biologically active leukotoxin, expresses a form of leukotoxin molecule which induces antibodies which specifically bind to leukotoxin, and contains no foreign DNA.

Another embodiment of the invention provides a method of inducing immunity to pneumonic pasteurellosis in ruminants. A bacterium is administered to a ruminant. Immunity to the bacterium is thereby induced. The bacterium expresses no biologically active leukotoxin, expresses a form of leukotoxin molecule which induces antibodies which specifically bind to leukotoxin, and contains no foreign DNA.

Yet another embodiment of the invention provides a feed for ruminants. The feed comprises a bacterium which expresses no biologically active leukotoxin, expresses a form of leukotoxin molecule which induces antibodies which specifically bind to leukotoxin, and contains no foreign DNA.

Even another embodiment of the invention provides a vaccine for reducing morbidity in ruminants. The vaccine comprises a *P. haemolytica* bacterium which expresses no biologically active leukotoxin, expresses a form of leukotoxin molecule which induces antibodies which specifically bind to leukotoxin, and contains no foreign DNA.

Still another embodiment of the invention provides a temperature sensitive plasmid. The plasmid replicates at 30° C. but not at 40° C. in *P. haemolytica*. Moreover, it is of the same incompatibility group as the plasmid which has been deposited at the ATCC with Accession No. 98895.

The present invention thus provides the art with tools for genetically manipulating an agriculturally important pathogen. It also provides useful mutant strains which can be used effectively to reduce morbidity among ruminants, such as cattle, sheep, and goats, due to *Pasteurella haemolytica*.

DETAILED DESCRIPTION

Figure 1:
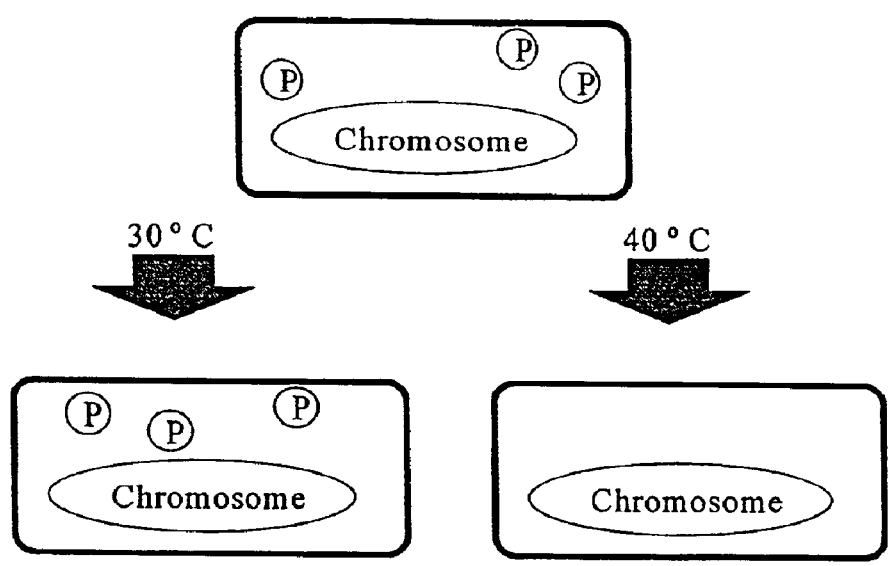
FIG. 1. Fate of temperature-sensitive plasmid in *Pasteurella hemolytica* after passage at 30° C. and 40° C.

It is a discovery of the present invention that a mutant form of leukotoxin is useful as a vaccine. The mutant form is made by a non-reverting mutant of *P. haemolytica*. Moreover, this mutant form has been found to be useful when administered to the tonsils, via the oral route, and via the nasal route. Thus extremely inexpensive and easy methods of vaccinating animals can be accomplished, simply by top dressing animal feed.

The mutant preferably is a deletion mutant. One such mutant leukotoxin protein made is about 66 kD, although other such mutants can be used, so long as the protein is long enough to be immunogenic, preferably at least 10, 15, or 20 amino acids long. It is believed that a longer deleted molecule is preferred to achieve a strong immune response. It is preferred that the mutant bacterium which makes the leukotoxin contains no exogenous genes, such as drug resistance genes, which can cause environmental and health problems if not contained. In addition, it is preferred that the mutation be a non-reverting mutation, such as a deletion mutation.

Mutant forms of leukotoxin of the present invention induce antibodies which specifically bind to leukotoxin. Antibodies which specifically bind to leukotoxin provide a detection signal at least 2-, 5-, 10-, or 20-fold higher than a detection signal provided with proteins other than leukotoxin when used in Western blots or other immunochemical assays. Preferably, antibodies which specifically bind to leukotoxin do not detect other proteins in immunochemical assays and can immunoprecipitate leukotoxin from solution. More preferably, the antibodies can be detected in an indirect hemagglutination assay and can neutralize leukotoxin.

Although the oral route is preferred for ease of delivery, other routes for vaccination can also be used. These include without limitation, subcutaneous, intramuscular, intravenous, intradermal, intranasal, intrabronchial, etc. The vaccine can be given alone or as a component of a polyvalent vaccine, i.e., in combination with other vaccines. Bacteria can be used in the vaccine to supply the mutant leukotoxin protein. The bacteria in the vaccine formulation can be live, lyophilized, lyophilized and reconstititued, or killed. Moreover, bacterial lysates, extracts or culture supernatants which contain the LtkA deletion protein can be used in the vaccine formulation. Purified protein can also be used, if desired. It can be formulated with other immunogenic proteins.

Also provided by the present invention is a temperature sensitive plasmid which replicates at 30° C. but not at 40° C. in *P. haemolytica*. Preferably the plasmid is of the same incompatibility group as pD80, i.e., it shares the same origin of replication. One such plasmid has been deposited at the ATCC with Accession No. 98895.

Vaccination with modified-live combination of *P. haemolytica* serotypes 5 and 6 protects against combined homologous virulent challenge extremely well, based on clinical signs, postmortem lesions, and results of bacterial culture. Animals which have been so vaccinated remain active, alert, afebrile, and on-feed. The vaccine can not only prevent death due to *P. haemolytica*, but can also reduce symptoms of pneumonic pasteurellosis, such as lung lesion volume, fever, decreased appetite, loss of lung ventilation capacity, fibrinous pleural effusion and/or adhesions, bacterial load, and depression.

The above disclosure generally describes the present invention. A more complete understanding can be obtained by reference to the following specific examples which are provided herein for purposes of illustration only, and are not intended to limit the scope of the invention.

EXAMPLE 1

Modified-Live Oral and Parenteral Vaccines Against Shipping-Fever and Pneumonic Pasteurellosis of Cattle, Sheep, and Goats Based on in-Frame Clean Deletions of the Leukotoxin Structural Gene of *Pasteurella haemolytica*

Materials and Methods

Mutagenesis of plasmid origin of replication. A 1.2 kb DNA fragment containing the putative pD80 origin of replication was amplified by PCR using the 4.3 kb ampicillin-resistance plasmid isolated from *P. haemolytica* serotype 1 strain NADC-D80 as template (1). Forward primer 5'-CCG GAT CCC CAA TTC GTA GAG GTT TC-3' (SEQ ID NO:1) and reverse primer 5'-CCG GAT CCG CTG AAA GCG GTC GGG GG-3' (SEQ ID NO:2) were used. The product was cloned into pCR2.1 vector (Invitrogen, San Diego Calif.) using the manufacturer's directions. A kanamycin-cassette was prepared by passage of pBC SK (Stratagene, La Jolla Calif.) containing a derivative of the Tn903 kanamycin gene (Pharmacia Biotech, Piscataway N.J.) cloned into the unique EcoR1 site through the *E. coli* strain PhaImtase to protect against PhaI-cleavage.

The cloned 1.2 kb insert (1 μg) was excised from pCR2.1 by EcoR1 digestion and ligated overnight to the EcoR1-digested PhaI-methylated kanamycin cassette (0.25 μg). The ligation mixture was concentrated by EtOH precipitation and electroporated (Gene-pulser, Bio-Rad, Redfield Calif.) into *P. haemolytica* serotype 1 strain NADC-D153 using 18 kv/cm and 1000 W.

Plasmid DNA was obtained from a kanamycin-resistant transformant which was 2.5 kb in size and cleaved into fragments of 1.2 and 1.3 kb when subjected to EcoR1. One μg of the plasmid was mutagenized with hydroxylamine for 1 hour at 65° C. as previously described (2).

Selection of temperature-sensitive plasmid origin of replication. The mutagenized plasmid was dialyzed overnight at 4° C. against TE, concentrated by ethanol precipitation, and electroporated into fresh NADC-D153 as described above. After 2 h recovery in Columbia broth (Difco Laboratories, Detroit Mich.), the cells were plated onto 10 Columbia blood agar base plates containing 50 μg/ml kanamycin and were incubated at 30° C. After 20 h, the plates were moved to 40° C. for an additional 6 h.

Colonies were selected which were atypically small and cloned to fresh kanamycin plates and were incubated overnight at 30° C. Growth from the clones was duplicated onto plates with and without kanamycin and incubated overnight at 40° C.

Clones which failed to grow on selective media at 40° C. but grew without selection were presumed to be temperature-sensitive for either plasmid maintenance or for expression of kanamycin. Growth from plates without antibiotic selection at 40° C. was passed to selective plates which were incubated overnight at 30° C. Clones which exhibited light or no growth on this passage were presumed to contain temperature-sensitive origins of replication. These clones were passed from the original 30° C. selective plate to fresh selective plates and to selective broth. The clones were rechecked by passage with and without selection at 40° C. and 30° C. Although each clone exhibited the correct phenotype, plasmid mini-preps from the broth cultures yielded small amounts of a 2.5 kb plasmid from only one of the cultures. The remaining clones were not examined further.

Construction of dual-origin temperature-sensitive shuttle vector. The temperature-sensitive origin of replication was excised from the above plasmid by EcoR1 digestion and then made blunt by treatment with Klenow fragment of DNA polymerase I and all four dNTPs. The fragment was ligated overnight at 4° C. with SmaI-digested pBC SK. The ligation mix was used to transform *E. coli* DH10-B (Life Technologies, Gaithersburg Md.).

Plasmid containing a 1.2 kb insert was recovered from a chloramphenicol-resistant colony. The plasmid was digested with SalI and ligated to SalI-digested kanamycin cassette overnight at 4° C. The ligation mixture was electroporated into *E. coli* DH10-B and plated onto kanamycin 50 μg/ml. Plasmid recovered from a kanamycin-resistant colony was digested with BssHII, made blunt as above, treated with calf alkaline phosphatase to remove the terminal phosphates, and ligated overnight at 4° C. with an approximately 900 bp blunt fragment containing the ColE1 plasmid origin of replication.

The ligation mixture was electroporated into *E. coli* PhaImtase (1) and plated onto kanamycin-containing plates. Plasmid was recovered from a kanamycin-resistant colony which yielded a single approximately 3.5 kb fragment with EcoR1-digestion and fragments of 2.2 and 1.3 kb with SalI-digestion. The plasmid was given the designation pBB80C. The plasmid was electroporated into *P. haemolytica* to confirm the temperature-sensitive origin of replication; it still supported bacterial growth on kanamycin at 30° C. but not at 40° C.

Cloning and manipulation of lktA. A 3.15 kb EcoRV fragment of *P. haemolytica* genomic DNA containing lktC and approximately 75% of the lktA coding region was ligated into the EcoRV site of pBB80C. The resulting plasmid was amplified in *E. coli* DH10-B and given the designation pBB80ClktA.

Plasmid pBC SK (0.25 μg, used to provide additional NaeI-sites in trans) was mixed with 0.25 μg pBB80ClktA and digested with NaeI for 18 h at 37° C. The resulting partially digested plasmid DNA was extracted with phenol-chloroform-isoamyl alcohol (PCI), precipitated with ethanol, ligated at 4° C. overnight, then re-extracted and precipitated. The ligation mixture was digested with PvuII, which cleaves both pBC SK and the 1035 bp NaeI fragment internal to LktA.

Five ng of the digested DNA was electroporated into *E. coli* PhaImtase and plated on Columbia blood agar base plates containing 50 μg/ml kanamycin. Plasmid DNA from selected transformants was screened by digestion of plasmid minipreps with EcoRV alone or together with NgoM1 (an isoschizomer of NaeI). A clone containing a 1035 bp deletion was selected and given the designation pBB80CΔlktA.

Recovery of leukotoxin mutants. Plasmid pBB80CΔlktA was electroporated into fresh *P. haemolytica* strain NADC-D153 at 18 kv/cm and 1000 W. The cells were allowed to recover 2 hours at 30° C. in 1 ml Columbia broth, then were plated 100 μl/plate on Columbia agar plates containing 50 μg/ml kanamycin. After 48 h incubation at 30° C., four colonies were passed to kanamycin plates containing 5% defibrinated bovine blood and were incubated overnight at 37° C. to select for single-crossover mutants. Four colonies from the 37° C. passage, 2 hemolytic and 2 non-hemolytic from each original transformant (16 total), were passed to Columbia broth without selection and incubated overnight at 30° C. to resolve the single-crossover mutations.

Growth from the 30° C. Columbia broth was struck for isolation onto blood agar base plates containing 5% defibrinated bovine blood and incubated overnight at 37° C. Growth was also passed to fresh Columbia broth successively for a total of 4 passages at 30° C. to further ascertain the rate at which kanamycin resistance was lost at 30° C. without selection. Isolated colonies from the first 30° C. passage were duplicated in an array on selective and on non-selective plates containing 5% defibrinated bovine blood.

A kanamycin-sensitive clone which demonstrated no detectable hemolytic activity on the non-selective plate was selected for further study. Additional strains of *P. haemolytica* obtained from the repository at the National Animal Disease Center were later subjected to similar treatment as above. These strains were isolated from pneumonic lung and included: NADC D632, ovine serotype 1; NADC D121, ovine serotype 2; NADC D110, ovine serotype 5; NADC D174, bovine serotype 6; NADC D102, ovine serotype 7; NADC D844, ovine serotype 8; NADC D122, ovine serotype 9; and NADC D712, ovine serotype 12.

Characterization of the putative leukotoxin mutant. To define the chromosomal deletion, DNA was amplified from whole cells of the putative leukotoxin mutant and from its parent strain NADC-D 153 by PCR, using primers nested within the EcoRV termini of the original 3.15 kb EcoRV genomic fragment. The products were electrophoresed on a 1.2% agarose gel both intact and after NgoM1 digestion.

To determine leukotoxic activity, log-phase culture supernatants from the putative mutant and its parent were prepared from Columbia broth 3 hour cultures. Two-fold dilutions of the supernatants were assayed using BL-3 target cells and MTT dye (7).

To determine the expression of the putative altered leukotoxin product, the culture supernatants, as well as a third culture supernatant from our original leukotoxin deletion mutant which produces no detectable leukotoxin, were concentrated approximately 15-fold using 30,000 mw ultrafilters (Centriprep, Amicon, Beverly, Mass.). The retentate was electrophoresed in duplicate on SDS-PAGE, and one gel was stained using Coomasie blue.

The second gel was blotted onto a nylon membrane for Western blot analysis. The membrane was washed, probed with anti-leukotoxin monoclonal antibody 601 (provided by Dr. S. Srikumaran, Lincoln Nebr.), labeled with anti-mouse IgG alkaline phosphatase-conjugated antibody (Sigma), and stained with nitro blue tetrazolium (Sigma).

*Pasteurella haemolytica* mutants of other than NADC D153ΔlktA serotype 1 were characterized by PCR analysis and growth characteristics on blood agar plates only. Their production of altered leukotoxin protein was not confirmed.

Results

The temperature-sensitive origin of replication derived from the endogenous *P. haemolytica* ampicillin-resistance plasmid proved to be a useful tool for the construction of deletion mutants in that organism. The origin of replication was assumed to reside within a non-coding region from nucleotides 3104 to 4293 of the native plasmid. The 1.2 kb PCR product of that region ligated to a 1.3 kb Tn903 kanamycin cassette resulted in a 2.5 kb product capable of the stable transformation of *P. haemolytica* as evidenced by less than 1% loss of plasmid after 100 generations in broth culture at 37° C. These data indicate that essential replication functions reside within that 1.2 kb region of the native plasmid.

Efficiency of transformation of *P. haemolytica* dropped about 10-fold after hydroxylamine mutagenesis, indicating perhaps the DNA was not particularly damaged. Nevertheless, 10 colonies which were atypically small were recovered after 20 hours at 30° C. and 6 hours at 40° C. Two of these colonies grew on selection at 40° C. and were discarded. Of the remaining 8 colonies, four were found to retain kanamycin-resistance after passage without selection at 40° C. These 4 colonies were presumed to contain plasmid which was temperature sensitive for the expression of kanamycin-resistance and were also discarded.

The remaining 4 colonies, presumed to contain plasmid which was temperature sensitive for maintenance, were recovered from the original 30° C. plate and passed again to 40° C. and 30° C. Although each grew well without selection at both temperatures, failed to grow with selection at 40° C., and failed to retain kanamycin-resistance after 40° C. passage, only one clone yielded sufficient plasmid for further study by a rapid alkaline lysis procedure. It was assumed the other 3 colonies also contained plasmid, but the rapid plasmid purification procedure failed to recover sufficient quantities to visualize on agarose gels. The plasmid yield from the positive clone was very low.

To facilitate subsequent isolation and cloning, a multiple-cloning site and a ColE1 origin of replication was added to the temperature-sensitive pD80 origin. The temperature-sensitive origin and a fresh kanamycin cassette were placed within the multiple-cloning site of pBC-SK, then the vector backbone was replaced with a <1 kb copy of the ColE1 origin. This approximately 3.5 kb plasmid, pBB80C, retains most of the unique restriction sites of pBC-SK, replicates efficiently in *E. coli*, and transforms *P. haemolytica* at 30° C. with moderate efficiency. In *P. haemolytica* the ColE1 origin fails to support replication, and plasmid maintenance is dependent on the mutated pD80 origin. In this situation, pBB80C failed to support growth on selective media at both 37 and 40° C. but supported moderate growth at 30° C. (FIG. 1).

Figure 2:
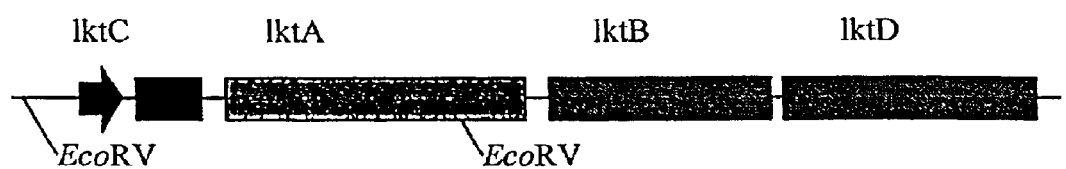
FIG. 2. The *Pasteurella hemolytica* leukotoxin operon with 3.15 kb EcoRV fragment. lktC, acylates leukotoxin structural gene to activate; LktA, leukotoxin structural gene; lktB/D, involved in leader-independent leukotoxin export.

To introduce an in-frame deletion within the coding region of *P. haemolytica* lktA by allelic exchange, an EcoRV fragment containing part of the leukotoxin operon was cloned into pBB80C, yielding pBB80ClktA. The clone extended approximately 500 bp upstream from the lktC start codon and included about 75% of lktA (FIG. 2).

Figure 3:
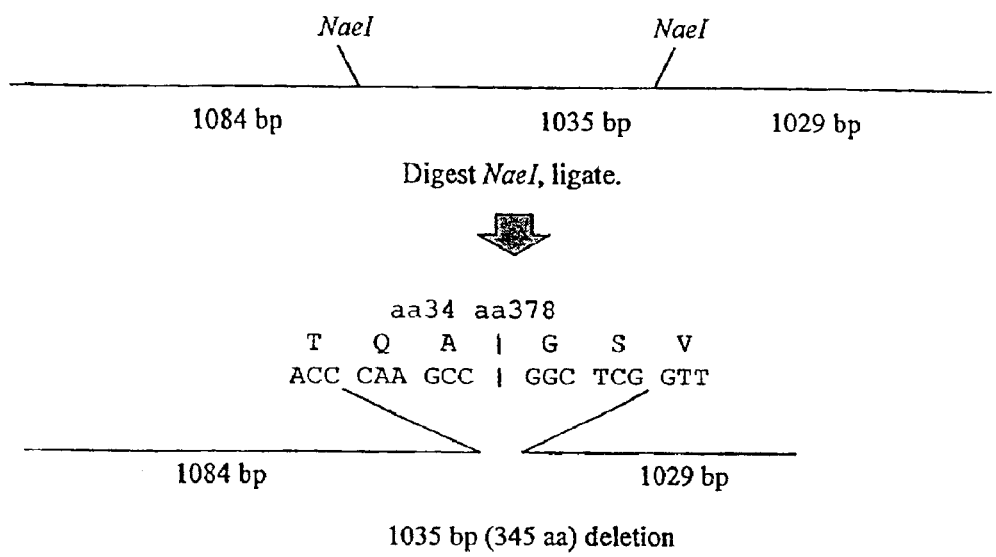
FIG. 3. In-frame deletion of 3.15 kb EcoRV fragment of lktCA using NaeI.

Within the EcoRV fragment are two NaeI sites which cleave between codons within lktA leaving blunt termini (FIG. 3). The NaeI sites are situated nearly evenly 1 kb apart within the EcoRV fragment. Digestion of pBB80ClktA with NaeI was complicated by the fact that NaeI is among a group of restriction endonucleases which show a dramatic site preference for cleavage (4). This enzyme requires simultaneous interaction with two copies of its recognition sequence before cleaving DNA. With certain enzymes of this type, the second copy may be supplied in trans, so it was chosen in this experiment to supply additional recognition sites to the digestion misture by adding pBC SK, which contains one site. Although this strategy resulted in incomplete cleavage after overnight digestion, a 1 kb fragment was evident in the mixture, indicating both NaeI sites had cleaved on some of the pBB80ClktA molecules.

Cleavage after ligation with PvuII, which is contained both in pBC SK and within the 1 kb NaeI fragment to be deleted, apparently eliminated most undesired products, because all transformants screened for pBB80CΔlktA contained the desired 1035 bp deletion. Each of these recleaved with NgoM1, indicating the new NaeI site was intact and the product should be in-frame to the lktA start codon.

Figure 4:
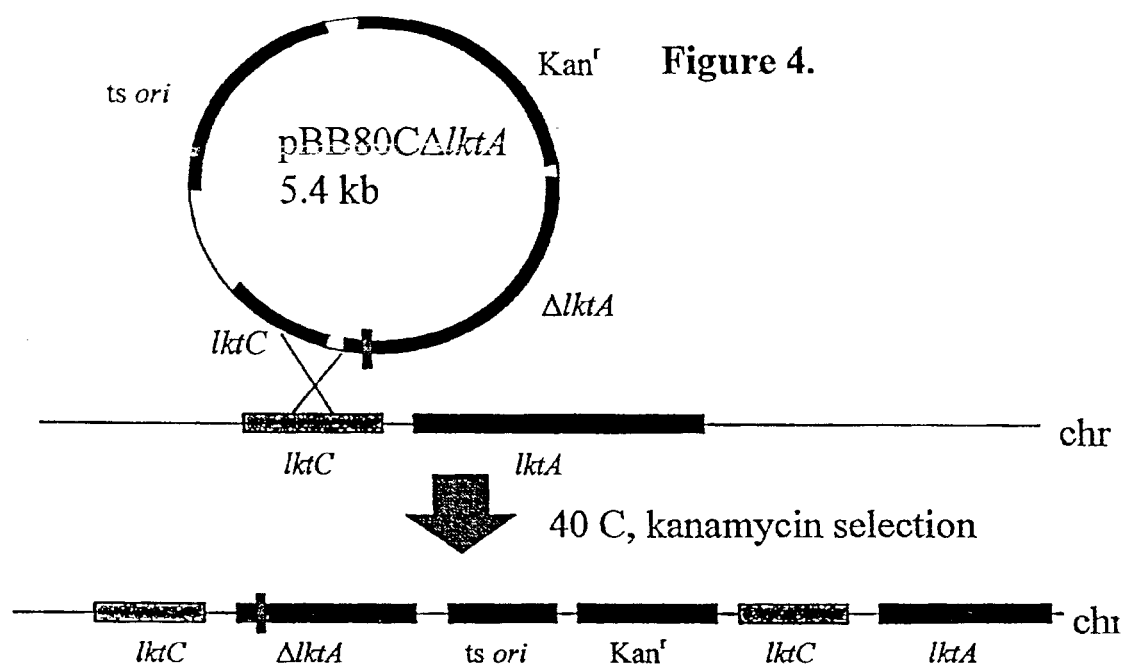
FIG. 4. Integration of replacement plasmid into chromosome.

*Pasteurella haemolytica* transformed with pBB80CΔlktA required nearly 48 hours to achieve good colony size at 30° C. Passage to 37° C. by simply streaking heavily on a kanamycin-containing plate resulted in numerous isolated colonies, some hemolytic and some not. These results are consistent with specific integration of the plasmid into the leukotoxin operon (FIG. 4). Since the replacement plasmid contained intact operon sequence upstream from the deletion, including the promotor, upstream single-crossover products were expected to express the entire operon normally. Downstream single-crossover products, however, were expected to contain two defective copies of lktA, since the C-terminal encoding 25% of lktA was not present on the replacement plasmid. One copy of the leukotoxin gene therefore would be expected to contain the 1 kb deletion and the other copy a truncated C-terminus. Hemolytic activity has previously been shown to be correlated with expression of active LktA (3, 5, 6).

Figure 5:
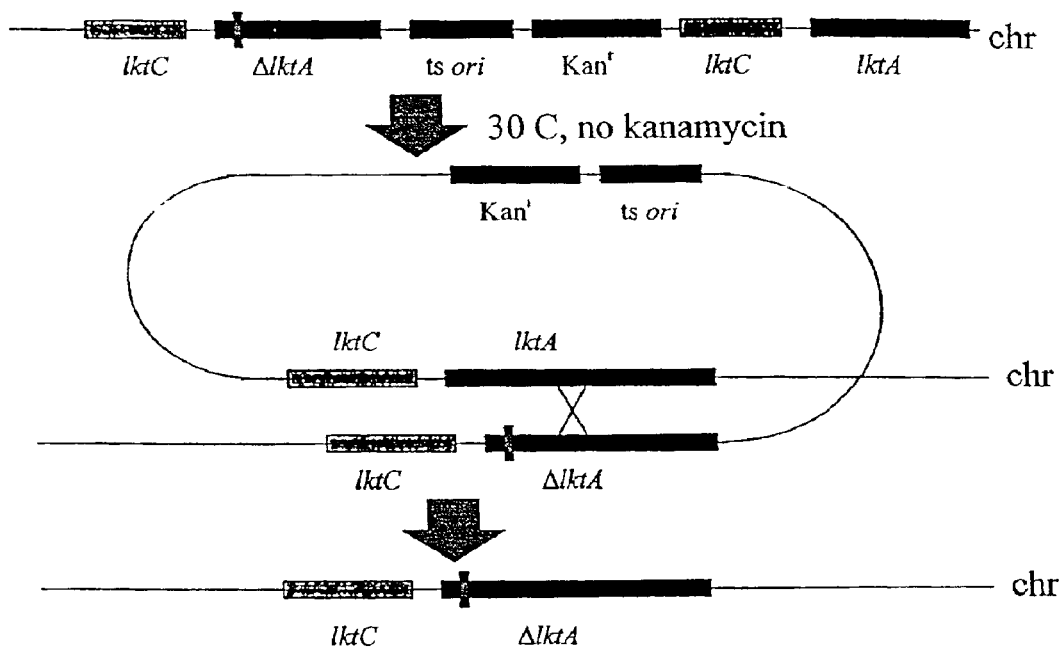
FIG. 5. Resolution of replacement plasmid from chromosome.

Passage of single-crossover products at 30° C. resulted in an unexpectedly low rate of plasmid resolution from chromosome. Previous work with pBB192C, a temperature-conditional plasmid derived from the *P. haemolytica* streptomycin-resistance plasmid, exhibited 90 to 99% reversion to kanamycin sensitivity after a single passage at 37 or 30° C. respectively. In this experiment, of 80 isolated colonies tested after one passage at 30° C., only two became sensitive to kanamycin. One of the two was non-hemolytic and was later shown to be a double-crossover mutant (FIG. 5). Further passage increased the percentage of kanamycin-sensitive CFU in non-selective cultures to nearly 50% after 4 passages. Many of these colonies exhibited a non-hemolytic phenotype and were probably double-crossover products.

To generate mutants of the other serotypes, 4–8 hemolytic single-crossover products were selected and passed at 30° C. for one or more passages in broth. Growth was struck for isolation on each passage, and non-hemolytic colonies were selected for testing by PCR and growth on kanamycin-containing media. In each case, non-hemolytic colonies which were kanamycin-sensitive were confirmed by PCR to be deletion mutants containing single NaeI sites.

We assume that pBB192C contains a more robust origin of replication than does pBB80C, as evidenced by the relative amounts of plasmid recovered from the respective cultures. If activity of an integrated plasmid origin destabilizes chromosomal replication, it would be expected that greater instability would be realized as plasmid origin activity increases. This could account both for greater resolving rates of pBB192C at 30° C. than at 37° C. and for the lower rates of resolving of pBB80C compared to pBB192. During construction of our first leukotoxin deletion mutant, a large number of single crossover products were obtained using suicide replacement plasmid (3), which contained ampicillin selection. Although both the homologous arms were similar in length to those of the current experiment, passage for even 100 generations resulted in no reversion to a hemolytic phenotype or loss of ampicillin-resistance. These data further indicate that it is the activity of plasmid origin which destabilizes the single-crossover products.

PCR products from the putative leukotoxin mutants and their parent strains were found to be 2 kb and 3 kb in size respectively, indicating a deletion had been introduced into their respective lktA. Digestion of the PCR products with NgoM1 revealed 2 bands of approximately 1 kb from the mutants and 3 bands of approximately 1 kb from the parent strains, indicating the deletions should be in-frame to LktA. Leukotoxin activity in culture supernatants against BL-3 target cells from the serotype 1 mutant was <1:2 compared to 1:1024 from the parent strain, indicating no detectable activity.

Figure 6:
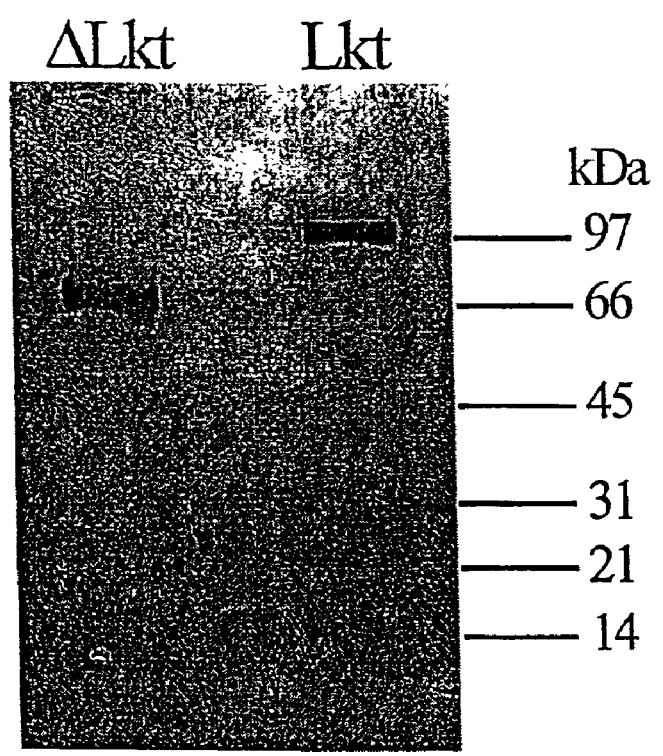
FIG. 6. Western blot of native leukotoxin and ΔlktA using anti Lkt monoclonal antibody.

A new protein of approximately 65 kDa was detected in the culture supernatant of this mutant by SDS-PAGE, consistent with the predicted molecular weight of the deleted product. By Coomasie staining, the new product exceeded the concentration of the native LktA protein produced by the parent strain grown and harvested alongside the mutant. The smaller size of this product may allow more rapid or economical expression of the gene. The product reacted with the neutralizing monoclonal antibody 601 at an apparent molecular weight of 66 kDa (FIG. 6). No reaction was observed at 101–104 kDa, the apparent molecular weight of the native product observed in the culture supernatant of the parent strain.

EXAMPLE 2

Assessment of Vaccine Efficacy in Small Ruminants After Intramuscular Injection of a Polyvalent Combination of *P. haemolytica* Serotypes 5 and 6

Materials and Methods

Vaccination of animals. Four lambs (Columbia, approximately 25 kg) and six goats (Toggenburg, approximately 15 kg) were colostrum deprived and raised at the National Animal Disease Center, Ames, Iowa. Two lambs and three goats were randomly selected and vaccinated with $4 \times 10^7$ CFU each of *P. haemolytica* NADC D110ΔlktA and NADC D174ΔlktA (serotypes 5 and 6 respectively) in 1 ml Earles Balanced Salt Solution (EBSS), pH 7.4. The suspension was delivered intramuscularly in the mid-cervical region. After three weeks, the animals were similarly revaccinated.

Ten days after the second vaccination all ten animals were challenged with $8.5 \times 10^7$ CFU each of the parent strains NADC D110 and NADC D174 mixed in a total volume of 5 ml EBSS instilled intratracheally at the tracheal bifurcation with a catheter. The inoculum was chased with 5 ml sterile EBSS. Five days after challenge all surviving animals were euthanized and necropsied.

Bacteria. *Pasteurella haemolytica* strains NADC D110 (serotype 5, ovine lung isolate) and NADC D174 (serotype 6, bovine lung isolate) were grown separately in Columbia broth (Difco Laboratories, Detroit Mich.) approximately 3 hours to late log phase, about $2 \times 10^9$ CFU/ml. Growth was diluted in EBSS 1:50 for the vaccine dose or 1:100 for the challenge dose. The two strains were mixed in equal volume and kept on ice prior to animal inoculation.

Samples and data collection. Sera were collected the day of the first vaccination, 2 weeks later, the day of challenge exposure, and the day of necropsy. Rectal temperatures were recorded for 3 days after each vaccination and twice daily from challenge exposure to necropsy. Clinical scores were subjectively assessed on the same schedule as rectal temperatures, based on degree of depression and appetite. At necropsy, lung specimens from 1 to 3 grams in weight were obtained from areas containing abnormalities, when possible, for bacterial enumeration. Swab specimens were obtained from trachea, kidney, and liver for bacterial isolation. Lung lesion volumes were estimated for each lobe of the lung, including both consolidated areas and those which appeared merely atelectic. Total lung lesion scores were expressed as a percentage where each lobe was adjusted for an approximation of its contribution to air exchange as follows: right cranial lobe, 6%; right cranial half of the middle lobe, 5%; right caudal half of the middle lobe, 7%; right caudal lobe, 35%; accessory lobe, 4%; left cranial lobe, 4%; left middle lobe, 6%; and left caudal lobe, 32%.

Sample processing. Sera were tested for *P. haemolytica* antibody by indirect hemagglutination (IHA) against serotypes 5 and 6 (all animals) and by leukotoxin neutralization (vaccinates only) using BL-3 cells and MTT dye (7, 8). Lung specimens were weighed, and EBSS was added to bring the tissue plus fluid volume to 10 times the weight. The specimens were ground to yield a homogenous suspension, and ten-fold dilutions were made in EBSS.

The dilutions (100 $\mu$l) were spread onto blood agar base plates containing 5% defibrinated bovine blood and incubated overnight at 37° C. Colonies exhibiting typical *P. haemolytica* morphology were enumerated, and 20 representative colonies (where available) were serotyped using specific antisera (9). Swabs were rolled onto one-third of fresh blood agar plates and then each side of a sterile loop was used to semi-quantitatively streak for isolation onto the remaining thirds consecutively.

Results

No local reaction was palpable or visible following either vaccination in any vaccinate. The first dose of vaccine elicited a febrile response, particularly in the sheep, which had a fever on day 2 and 3 which peaked at 40.3° C. on day 3. The second injection elicited no clinical response.

Prior to vaccination, the animals had a low IHA titer against both serotypes 5 and 6 of *P. haemolytica* (Table 1). After the first vaccination, the vaccinates' titer increased over 8-fold against both serotypes. No response was evident after the second dosage. Only a slight increase in antibody titer, about 50%, occurred after challenge exposure. The control animals' titer increased slightly, about double, prior to challenge exposure. Between the time of challenge exposure and necropsy, the one surviving control sheep increased its titer against both serotypes by about 32-fold.

Leukotoxin neutralization titers in the vaccinates increased variably. Both lambs and two goats seroconverted (increased at least 4-fold) after the first vaccination; one of the animals also seroconverted to the second dose. One goat remained seronegative throughout the study.

Following challenge, none of the vaccinates had a fever at any time. They remained alert and eating all their food until necropsy. The control animals had a fever the day after exposure averaging 40.7° C. All control goats and 1 control sheep died overnight between the first and second day after exposure. The remaining control sheep remained febrile, anorexic, and depressed until necropsy.

Inspection of the vaccine injection site at necropsy revealed no detectable reaction in the muscle. Slight subcutaneous discoloration about 1 cm in diameter due to hemorrhage was detected in both sheep and two of the three goats.

Lung lesion volume of the vaccinates, corrected for ventilation capacity of each lobe, averaged 3.5% (Table 2). One goat had 95% of its accessory lobe with moderately firm consolidation from which $1.3 \times 10^6$ CFU/g (equally of serotypes 5 and 6) were recovered. The remaining lung lesions were soft, consistent with atelectasis.

Of 19 lung specimens quantitatively cultured, 5 yielded *P. haemolytica*. Two animals yielded no *P. haemolytica* from their lung. Two yielded from $2 \times 10^3$ to $7 \times 10^3$ CFU/g from their right cranial lobes or cranial half of the middle lobe only. The animal with accessory lobe involvement also yielded $1 \times 10^3$ CFU/g from the right caudal half of its middle lobe and moderate growth from its tracheal swab. All other tracheal swabs from vaccinates were culture negative, as were swabs from liver and kidney.

One sheep had tight adhesions of visceral to parietal pleura and to the pericardium ventrally on both right and left sides involving all lobes. This sheep contained only minor lesions of atelectasis and yielded only $2 \times 10^3$ CFU/g from its right cranial lobe; both other lobes cultured were negative.

Lung lesion volume of the controls (corrected for ventilation capacity of each lobe) averaged 52% (Table 2). The four animals which died contained large amounts of fibrinous pleural effusion and fibrinous pleural adhesions. The lung lesions were firm or moderately firm, and emphysematous and/or crepitous areas were evident. The sheep which survived until the time of necropsy contained about 100 cc pleural effusion and a large (about 250 cc) fibrous mass occupying the plerual space over the right cranial and middle lobes.

The lung lesions consisted primarily of firm fibrinous consolidation in this animal. Of 17 cultured lung specimens, all yielded *P. haemolytica* from as few as $2.5 \times 10^4$ CFU/g to $4 \times 10^9$ CFU/g. The geometric mean count for the four animals which died acutely was $2.5 \times 10^8$ CFU/g; the surviving sheep had a mean count of $2.5 \times 10^5$ CFU/g. Tracheal swabs from the four animals which died yielded heavy growth of *P. haemolytica*. The surviving sheep yielded light growth from its trachea. Liver swabs of all four and kidney swabs of two of the animals which died yielded *P. haemolytica*. The surviving sheep was culture negative in both liver and kidney.

Serotyping of isolates from lung revealed that the few colonies recovered from vaccinates were of serotype 5, except for the actively infected accessory lobe of one goat which yielded equal amounts of both serotype 5 and 6. Control animals tended to yield a mixture of serotypes from each lobe, but the mixture varied widely from lobe to lobe in the animals which died acutely (e.g. 95% of serotype 5 in the right cranial lobe to only 5% of serotype 5 in the right caudal lobe). Isolates recovered from kidney or liver tended to be homogenous with respect to serotype in any given animal, but two animals contained serotype 5 in these tissues, and the other two contained serotype 6.

The first dose of vaccine can induce a febrile response. The lack of a febrile response and immune response from the second dose implies that substantial immunity is conferred by the first dose. The second dose was apparently quickly dealt with by the immune system and did not develop sufficient antigenic mass to elicit an anemnestic response. The dosage of organisms delivered in the vaccine (nearly $10^8$ CFU) may have exceeded that necessary to confer sufficient immunity. Modified-live vaccines typically would be delivered at a lower dose, perhaps $10^5$ to $10^7$ CFU. The failure of the second dosage of vaccine to stimulate further antibody, as measured by IHA, may indicate that two doses were unnecessary and that a single dose would have been sufficient.

The reactions observed at the vaccine injection sites were extremely minor and did not involve muscular tissue, consistent with findings using leukotoxin negative mutants of serotype 1 in cattle. This contrasts greatly with the response of leukotoxin positive strains given intramuscularly to cattle, which evidence large swellings and necrosis in the area, often opening through the overlying skin. It is likely that little or no local adverse reaction would occur with subcutaneous or intradermal vaccination, an alternative that may also tend to reduce the febrile response to vaccination.

Thus polyvalent intramuscular vaccine elicited marked immunity in sheep and goats against polyvalent challenge. Adverse reactions were limited to a febrile response after injection which might be controlled by reduced vaccine dosage or an alternative route of administration.

EXAMPLE 3

Assessment of Vaccine Efficacy in Cattle After Oral Administration and After Intramuscular Injection Materials and Methods Vaccination of animals. Sixteen dairy-type calves, approximately 150 kg, were obtained from a local dairy and housed at the National Animal Disease Center, Ames, Iowa. The calves were randomly assigned to one control group of six and two vaccinate groups of 5. Each group was separately housed under similar conditions to prevent spread of vaccine organism between groups.

To each calf in one group of vaccinates was subcutaneously administered in the mid cervical region 1 ml of EBSS containing $1\times10^7$ CFU P. haemolytica serotype 1, NADC D153ΔlktA in-frame deletion mutant on day 0. These calves were revaccinated similarly with $7.0\times10^6$ CFU in 1 ml EBSS on day 21. The other group of vaccinates was fed a pelleted ration (Growena, Ralston Purina, St. Louis Mo.) onto which 50 ml total volume of a fresh broth culture containing $1\times10^9$ CFU/ml NADC D153ΔlktA in-frame deletion mutant was poured on day 0. The calves were similarly fed 50 ml of $7\times10^8$ CFU/ml on day 21.

On day 28 all calves were challenged intratracheally with 25 ml of the parent P. haemolytica in EBSS at $2\times10^7$ CFU/ml using a catheter placed at the tracheal bifurcation. The challenge was chased with 25 ml sterile EBSS. Calves which survived challenge were euthanized 4 or 5 days after challenge and necropsied.

Bacteria. Pasteurella haemoltica strain NADC D153 and its leukotoxin mutant were grown in Columbia broth approximately 2.5 hours to mid log phase, about $1\times10^9$ CFU/ml. Growth was diluted 100-fold in EBSS for injection or 50-fold for challenge. Growth was used unwashed and undiluted for oral administration. All preparations were kept on ice prior to animal inoculation.

Samples and data collection. Sera were collected 3 days prior to the day of the first vaccination, 3 weeks later, the day of challenge exposure, and the day of necropsy. Rectal temperatures were recorded for 3 days after each vaccination and twice daily from challenge exposure to necropsy. Clinical scores were subjectively assessed on the same schedule as rectal temperatures, based on degree of depression and appetite.

At necropsy, lung speciments were obtained and treated as described in Example 2, above.

Sample processing. Sera were tested for P. haemolytica antibody by IHA against serotype 1 and by leukotoxin neutralization using BL-3 cells and MTT dye. Lung specimens were weighed, and EBSS was added to bring the tissue plus fluid volume to 10 times the weight. The specimens were ground to yield a homogenous suspension, and ten-fold dilutions were made in EBSS. The dilutions (100 ml) were spread onto blood agar base plates containing 5% defibrinated bovine blood which were incubated overnight at 37° C. Colonies exhibiting typical P. haemolytica morphology were enumerated and, where available, 10 representative colonies were serotyped using specific antisera. Swabs were rolled onto one-half of fresh blood agar plates, and then each side of a sterile loop was used to semi-quantitatively streak for isolation onto the remaining two quarters consecutively Results No local reaction was palpable or visible following either parenteral vaccination. None of the calves exhibited a febrile response after the first parenteral or oral vaccination. One parenterally vaccinated calf exhibited a transient (1 day) fever of 40.4° C. after the second dose; no adverse reaction was noted with any of the remaining calves.

Prior to vaccination, the animals had a low IHA titer against serotype 1 P. haemolytica (Table 3). After the first vaccination, the antibody titer in calves fed the vaccine increased at least 8-fold over their prevaccination titers. The second oral dose did not increase, and in some cases titers dropped 2-fold. Titers of parenterally vaccinated calves increased only about 2-fold after the first dose of vaccine, during which time similar titer increases occurred in the control calves. The second dose of parenteral vaccine elicited additional antibody response in the parenteral vaccinates, seroconverting (4-fold increase) 3 of these 5 calves.

Leukotoxin neutralization titers were relatively high in most calves prior to vaccination (Table 3). Two orally vaccinated calves seroconverted after the first vaccine dose. One parenterally vaccinated calf seroconverted after the second vaccine dose. Overall, antileukotoxin titers increased in both vaccinated groups on successive bleedings. Antileukotoxin titers of control calves tended to decrease on successive bleedings.

Following challenge, some but not all of the parenteral vaccinates exhibited fevers under 41° C.; the oral vaccinates remained afebrile. All the vaccinates remained alert and on-feed. One control animal died the third day after challenge. Another was euthanized on day 3 nearly moribund. Two of the remaining control calves were depressed and off-feed and maintained a fever until euthanasia on day 4 or 5. One of these calves was recumbent and thumping at the time of euthanasia. The remaining 2 control calves became afebrile the third day after challenge. They resumed eating and were deemed alert.

Lung lesion volume, corrected for ventilation capacity of each lobe, averaged 4.4% for orally vaccinated animals, 7% for those subcutaneously vaccinated, and 32% for unvaccinated controls (Table 4). Lung lesions of both vaccinated groups were predominantly soft, consistent with atelectasis. Localized areas of firm consolidation were noted in 2 of the orally vaccinated calves and 4 of the parenteral vaccinates, with limited pleuritis and moderate pleural adhesions in two animals of each group. These firm areas were confined to fractions of single lung lobes in each case. Unvaccinated controls had multiple lung lobes which contained a substantially higher percentage involvement with firm, fibrinous consolidation associated with edema and extensive fibrinous pleuritis. Three of the six control animals contained a large amount of pleural effusion.

Bacterial culture of lung specimens showed that 2 orally vaccinated calves and 1 parenterally vaccinated calf were culture negative in all tested lobes. The remaining vaccinates tended to have one or two specimens which yielded substantial amounts of P. haemolytica, up to $5 \times 10^7$ CFU/g. The remaining lobes were either culture negative or contained low amounts of P. haemolytica, about $10^3$ CFU/g. Unvaccinated control animals yielded multiple specimens with high numbers of P. haemolytica, over $10^7$ CFU/g with many between $10^9$ and $10^{10}$ CFU/g. Nasal swabs yielded P. haemolytica from 1 parenterally vaccinated calf and 4 control calves. Tracheal swabs were culture-positive for P. haemolytica in 4 control calves, 1 of which was nasal culture-negative. Pleural fluid was culture positive in 3 control calves. All vaccinates were culture-negative from trachea and pleural fluid. No P. haemolytica were recovered from liver or kidney of any calf. All P. haemolytica were β-hemolytic, and those tested were serotype 1.

Thus, vaccination with the modified-live P. haemolytica protected against virulent challenge, whether the vaccine was administered subcutaneously or orally after top-dressing feed.

Adverse reactions to vaccination were limited to one animal exhibiting a transient fever after the second subcutaneous injection of vaccine. No local irritation or swelling was evident nor any postmortem abnormalities at the injection site, and no clinical abnormalities were noted in any animal, whether injected or fed vaccine. The vaccine dosage used for injection was about 4-fold lower than that used in Example 2, above.

Seroconversion by IHA was impressive for animals orally vaccinated. All animals' titer increased at least 8-fold after the first exposure. Less impressive was seroconversion after subcutaneous injection. No animals seroconverted after the first dose, and only 3 of 5 sevoconverted after the second dose. The IHA procedure has been found useful as a measure for animals' prior experience with P. haemolytica of specific serotypes (10–13). Its utility for predicting resistance to disease is unclear, however (14–16). While some researchers find a correlation between IHA titers and disease, others find none. If one assumes that the serotype-specific antigens employed in the IHA procedure are not those involved in humoral protection, the discrepency can be explained. Vaccination could elicit an IHA response without significant protection or, conversely, elicit little IHA response but substantial protection. In either case, it is not surprising that oral exposure would elicit a good response, assuming that such exposure is sufficient to qualify as "prior experience." The subcutaneous vaccination, while apparently effective, elicited a relatively minor IHA response. Our prior experiment in small ruminants using IM injection resulted in substantial IHA responses to both P. haemolytica serotypes 5 and 6. Perhaps the route of exposure directed the former to a primarily cell-mediated response and the latter to a more humoral response.

Antileukotoxin titers were not impressive in either group, as only 3 of 10 vaccinated animals seroconverted after vaccination. Antileukotoxin titers were substantial prior to vaccination, however, and may have contributed to a decreased response. These preexisting titers may have been due to previous colonization by serotype 2 P. haemolytica, the most common commensal P. haemolytica in calves' nasal passages. Alternatively, it is possible that replication of P. haemolytica after vaccination was not great, perhaps because the bacteria were readily handled by the immune system, and therefore little antigenic mass of leukotoxin was elaborated. Finally, there is the possibility that the altered leukotoxin protein, although designed to leave immunodominant epitopes, is not particularly adept at stimulating a neutralizing response even if it is immunogenic. There is little doubt, however, that some leukotoxin neutralizing antibody was produced in response to vaccination.

The multiple large areas of firm lung consolidation in unvaccinated animals at necropsy and the relatively large concentration of P. haemolytica in those areas indicate an active infection which spread from the initial site of inoculation. In contrast, the vaccinates (except the 3 with essentially clean, culture-negative lungs) had relatively smaller areas of consolidation confined to single lung lobes which contained moderately high numbers of P. haemolytica. Other lobes of these animals were either culture-negative or contained low to moderate numbers of bacteria. These data may indicate that the infection was active primarily at the site of inoculation and bacteria were having difficulty establishing in other portions of the lung. The culture results from tracheal specimens might support that conclusion, since 4 of the 6 control animals but none of the vaccinates yielded P. haemolytica from this source, which indicates the infection was not well contained in most of the controls.

The data are clear that both subcutaneous administration and oral administration of the modified-live vaccine were of significant benefit to animals intratracheally challenged with wild-type P. haemolytica serotype 1. Manipulation of dosage or use of intramuscular injections might further improve the efficacy of parenterally administered vaccines.

The orally administered vaccine was markedly efficacious. The necessary dose in this case is likely some threshold level which is sufficient to cause colonization of the upper respiratory tract or palatine tonsils. Although conceivable, it is unlikely the dosage was effective due to passage into the gastrointestinal system.

Even $10^{10}$ CFU of P. haemolytica passing into the rumen would be a relatively small number of organisms, and the possibility that these bacteria could compete against the rumen or intestinal flora and multiply is remote. Still, if the gut were to respond and there is a mucosal immune system link in cattle, one might expect the response to be beneficial. These possibilities might be investigated using genetically marked P. haemolytica such as a rifampicin-resistant strain for which colonization can be detected with great sensitivity (7, 11).

The theory behind the oral vaccine is that animals naturally infected with P. haemolytica serotype 1 develop resistance to subsequent nasal colonization by serotype 1 organisms. They also develop systemic antibodies against P. haemolyica and, variably, against leukotoxin. An avirulent organism which is proficient at colonization of nasal passages or palatine tonsils might elicit similar resistance or resistance to pulmonary challenge without the possibility of causing pneumonic pasteurellosis.

It is even possible that passive protection might occur in some cases by competitive exclusion of virulent P. haemolytica. Delivery by carriage on feedstuffs is possible because the palatine tonsils sustain long-term colonization by P. haemolytica (18, 19). These sites also are in the path of incoming feed. Often course feedstuffs such as hay stems are found within the larger sinuses of the palatine tonsils, indicating that exposure to feed is significant.

We conducted preliminary experiments to test the ability of feed to deliver P. haemolytica to palatine tonsils or nasal passages using a rifampicin-resistant strain of P.

*haemolytica*. Calves fed infected feed became colonized in both tonsils and in nasal passages.

In summary, protection against virulent challenge was conferred by subcutaneous or oral administration of a modified-live *P. haemolytica* vaccine. In this experiment, oral administration elicited greater antibody responses and slightly greater protection. An additional potential benefit of vaccination via feed is that calves would not need to be caught to be vaccinated, thereby reducing stress for both the calf and the operator. A potential caveat is that at least some calves must eat or at least browse through the inoculated feed to become colonized. Calves which do not partake of the feed may later become immune after exposure to calves which did partake.

EXAMPLE 4

Preliminary Assessment of Safety and Efficacy of Orally-Administered Vaccine for Calves Already in Typical Marketing Channels This experiment was designed to test the efficacy of an experimental pulmonary vaccine produced by personnel at Texas A & M University. Within that experiment, and balanced between the groups of calves utilized by Texas A & M, was our smaller experiment involving 18 head of calves. Our experiment was designed to see if feeding our vaccine strain to calves in the early stages of typical marketing channels would result in colonization, elicit an immune response, and possibly reduce the incidence of shipping fever.

A field experiment was conducted in the Fall of 1997 with 105 steer calves (average 207 kg) procured from local sales barns by an Order-Buyer in eastern Tennessee. Although the primary objective of the experiment was to test an experimental vaccine by Texas A&M University, 18 calves were fed the in-frame leukotoxin mutant 4 days prior to shipment to a feedlot in Texas about 1600 km away. The day after purchase, the calves arrived at an order-buyer barn where they were ear-tagged, vaccinated against clostridia, infectious bovine rhinotracheitis, and parainfluenza-3 virus, wormed with ivermectin, and castrated by banding. Blood was collected for serum, rectal temperatures were recorded, and nasal mucus specimens were collected.

Odd numbered calves were vaccinated with the experimental Texas A&M preparation. Nine odd- and nine even-numbered calves were separated into a pen approximately 20' by 40' which contained a 12' feed bunk and a source of fresh water. A suspension of *P. haemolytica* NADC-D153ΔlktA (100 ml) was poured onto 35 kg of a commercial calf ration (Growena, Ralson Purina, St. Louis Mo.) and 15 kg of fresh grass hay. The bacteria were grown on 10 Columbia agar plates overnight at 37° C. after spreading inoculum for confluent growth. Growth was harvested into EBSS to a density approximating $2\times10^9$ CFU/ml, and the resulting suspension was placed on ice until the calves were penned, whereupon 150 ml was top-dressed onto the above feed.

Four days after feeding the vaccine, the calves were loaded onto a truck and transported to Bushland, Tex., where an experimental feedyard is operated jointly by the USDA Agricultural Research Service and by Texas A&M University. Upon arrival the next day the calves appeared exhausted, as is typical of shipping this distance. The calves were run through the chute and rectal temperatures were recorded. The calves were then sorted into 6 groups and allowed to rest overnight. The next day, the calves were again run through the chute. Blood and nasal mucus was collected, rectal temperatures were recorded, and weights were taken. Many of the calves were febrile (over 40° C.) with nasal discharge and loose stool.

The protocol called for treating calves for shipping fever with antibiotic on the second consecutive day of fever using tilmicosin (Micotil, Eli Lilly, Indianapolis Ind.). Calves not responding within 2 days of treatment were to be treated with long-acting tetracycline (LA-200, Pfizer Inc., New York N.Y.). It was deemed expedient, considering the number of hot calves, to run all calves through the chute daily for 4 days to record all rectal temperatures. Serum, nasal mucus, weights, and rectal temperatures were then collected weekly (counting from the day after arrival) for 4 weeks, as described above.

The second day after arrival, 55 calves were treated using tilmicosin. Additional calves were treated subsequently until 22 days after arrival, bringing the total number treated to 84% of surviving animals. Ten total animals died within 4 days of arrival, 6 given the Texas A&M product and 4 non-vaccinates. No animals given the oral vaccine died.

Postmortem observations revealed fibrinous pneumonia in all ten dead animals, and *P. haemolytica* was recovered from all lungs along with *P. multocida* in a few lungs. Serotyping of lung isolates revealed that 9 calves died of pasteurellosis by serotype 1 and 1 calf by serotype 6. No statistically significant differences were noted in morbidity (as judged by treatment) between the orally-vaccinated, Texas A&M-vaccinated, or control animals (78%, 84%, and 87% respectively). Nor was the difference in mortality significant (11.5% of non-orally-vaccinated versus 0% of orally-vaccinated calves, $p>0.05$).

Antibody titers (measured by IHA against serotype 1 *P. haemolytica*) increased significantly ($p<0.01$) between samples taken at the order-buyer barn and those taken on arrival at the feedyard for both orally-vaccinated and Texas A&M vaccinated calves compared to non-vaccinates. Overall, the calves gained 29 kg between purchase and the termination of the experiment after 28 days in the feedyard. One group, orally-vaccinated calves which did not receive the Texas A&M vaccine, gained significantly more weight than any other group ($p<0.01$, $n=9$) at 40.2 kg. All other groups did not significantly differ in this parameter.

*Pasteurella haemolytica* serotype 1 and, to a lesser extent, serotype 6 were recovered from nasal mucus of most calves one or more times at the feedyard. The groups did not differ significantly in shedding the organism. Some but not all calves which received the oral-vaccine shed the mutant organism in one or more nasal mucus specimens during the first week at the feedyard, indicating that the inoculum was sufficient to colonize their upper-respiratory tracts under these conditions.

This experiment demonstrates that our experimental oral vaccine can be delivered in feed at an order-buyer barn prior to shipment to the feedyard and thereby colonize and elicit an immune response within 1 week. Morbidity and mortality in the current experiment were unusually high. In addition to frequent isolations of *P. haemolytica*, respiratory coronavirus and *P. multocida* isolations were common. The number of calves from which coronavirus was isolated was unusually high and may account for the unusually heavy morbidity and the frequent diarrhea observed. The number of calves requiring retreatment was also unusual, suggesting that bacteria other than *P. haemolytica* played a significant role in the outbreak.

Tilmicosin is an antibiotic with a narrow spectrum of activity, targeted and advertised primarily to combat *P.* haemolytica. Given that bacteria other than *P. haemolytica* and viruses such as respiratory coronavirus were prevalent, it is not particularly surprising that the monovalent vaccines against *P. haemolytica* did not significantly reduce morbidity. However, none of the orally-vaccinated calves succumbed to pneumonic pasteurellosis compared to 11.5% of the others, suggesting that the vaccine played a role in reduction of mortality. The substantially greater weight gain of calves given only the oral vaccine further supports the conclusion that the vaccine reduced disease in these calves. Administration of the Texas A&M product together with the oral vaccine may have resulted in a reduction in the response to one or both products or in responses deleterious to disease-resistance and thereby reduced the benefit conferred by the oral vaccine alone.

EXAMPLE 5

Ability of the *P. haemolytica* Serotype 1 Leukotoxin In-Frame Deletion to Colonize Nasal Passages of Calves Stressed by Concurrent Bovine Herpes Virus Type 1 Infection

*Pasteurella haemolytica* serotype 1 is recovered sporadically in relatively low amounts from nasal mucus specimens of normal healthy calves. After stress or respiratory viral infection, *P. haemolytica* serotype 1 can proliferate explosively in nasal passages to become the predominant flora. Very high amounts of bacteria are shed in nasal mucus of such calves. It is believed that these high numbers of bacteria are inhaled or aspirated into susceptible lung to result in pneumonic pasteurellosis. Thus, this experiment was designed to obtain preliminary data on whether leukotoxin deletion mutants of *P. haemolytica* can colonize nasal passages under these conditions and, if so, whether they might competitively exclude colonization by wild-type *P. haemolytica*. Both serotype 1 and serotype 6 organisms were used because both are known to cause fatal fibrinous pneumonia in calves.

Materials and Methods

Vaccination of animals. Eight crossbred dairy-type calves, about 150 kg, were purchased from a local dairy and maintained at the NADC. The calves were separated randomly into 2 groups of 4 each such that no contact could occur between the groups. The calves were allowed to acclimate for 10 days prior to initiation of the experiment.

Infectious bovine rhinotracheitis virus (Coopers strain, kindly provided by National Veterinary Services Laboratories) was aerosolized into each calf's nostrils on inspiration, according to instructions provided by NVSL for challenge, resulting in a final dosage of $10^{9.4}$ TCID$_{50}$/nostril. After exposure to virus, one group of 4 calves were fed a palatable feed concentrate onto which 10 ml/calf of a mixed suspension of *P. haemolytica* D153ΔlktA and D174ΔlktA (serotypes 1 and 6 respectively) at $2 \times 10^9$ total CFU/ml was poured. The other group was fed uninoculated ration.

Five days after exposure to virus, the fed group was exposed by intranasal injection to 1.5 ml/nostril of *P. haemolytica* (mixture as above) at $2.7 \times 10^8$ total CFU/ml. Six days after exposure to virus, all groups were exposed by intranasal injection to a mixture of wild-type *P. haemolytica* D153 and D174 at $5 \times 10^8$ total CFU/ml.

Sample collection and analysis. Nasal mucus specimens were collected on the day of exposure to virus, and 3, 4, 5, 6, 7, and 10 days after virus exposure. Serum was collected the day of exposure and 10 days later.

On the tenth day after exposure to virus, all calves were euthanized, and the lungs were examined grossly. Rectal temperatures were recorded daily from the day of exposure to virus until euthanasia. Serum was tested for antibody against both serotype 1 and serotype 6 *P. haemolytica* by IHA.

Nasal mucus was diluted in 10-fold increments and spread onto blood agar base plates containing 5% defibrinated bovine blood. After overnight incubation, *P. haemolytica* were identified and enumerated, and 20 representative colonies were serotyped by a rapid plate agglutination procedure.

Results

Most calves were febrile within 3 days of virus-exposure, and peak fevers occurred on day 4 at 40.5° C. Only 3 calves remained febrile more than one week, and all became afebrile by 10 days after virus exposure.

All calves were culture-negative for *P. haemolytica* in nasal mucus the day of virus-exposure. One calf fed *P. haemolytica* leukotoxin mutants shed non-hemolytic serotype 1 organisms in its nasal mucus specimens starting 3 days after virus-exposure and continued to shed leukotoxin mutants until euthanasia. The remaining 3 fed calves remained culture-negative for *P. haemolytica* until day 6, one day after intranasal exposure to the mixture of leukotoxin mutants. These calves shed non-hemolytic *P. haemolytica* on days 6, 7, and, with one exception, day 10 (Table 5). The calves not deliberately exposed to *P. haemolytica* until day 6 remained culture negative for the organism until day 7, whereupon they shed mixtures, with one exception on day 10, of serotype 1 and serotype 6 hemolytic *P. haemolytica*.

Three animals exposed to mutant *P. haemolytica* seroconverted (4-fold or greater increase in titer) to both serotypes 1 and 6 between the time of virus-exposure and euthanasia. The fourth animal had a two-fold titer increase against both serotypes. The remaining animals either increased 2-fold or maintained a constant titer during that period.

The lungs at postmortem were mostly unremarkable. Calf 30, unexposed to leukotoxin mutants, had firm consolidation throughout its right caudal half of the middle lobe with 5% involvement of the cranial half. Calves 17 and 18 had minor lesions of consolidation involving 5% or less of 2 and 3 lung lobes respectively. No abnormalities were noted in the remaining calves.

*Pasteurella haemolytica* leukotoxin mutants were capable of colonizing the nasal passages of calves which were concurrently infected with IBR virus. Such colonization did not prevent or even reduce experimental superinfection with wild-type *P. haemolytica*. Judging by numbers of *P. haemolytica* shed in nasal mucus, it appears the leukotoxin mutants were less robust in nasal colonization. The wild-type bacteria colonized at levels about 10-fold higher than did the mutants whether by themselves or together. Nevertheless, the leukotoxin mutants were able to maintain a substantial level of colonization even in the presence of wild-type *P. haemolytica*, indicating that the bacteria were still quite robust. In fact, mixtures of wild-type parent strains and leukotoxin mutants passed in vitro in Columbia broth for 100 generations resulted in a population slightly enriched for leukotoxin mutants, indicating that the leukotoxin mutants compete very well with wild-type under those conditions. Whether it is possible to superimpose infection with leukotoxin mutants in the face of substantial colonization by wild-type *P. haemolytica* is not known. Perhaps the leukotoxin mutants maintained their infection because they already had a foothold in the nasopharynx.

Our previous work with *P. haemolytica* infections using an IBR virus model indicates that bacterial infection of the nasopharynx (specifically, the palatine tonsils) does not necessarily translate into explosive colonization of the nasal passages. Some calves which were known carriers of *P. haemolytica* serotype 1 in the palatine tonsils failed to become colonized in the nasal passages even though the nasal passages were susceptible, as demonstrated by intranasal inoculation. Other similar calves of probable but unconfirmed carrier status did become colonized under similar conditions. This seeming paradox, infection in the pharynx which may or may not extend into adjacent susceptible nasal passages, is not easy to explain. Perhaps the ciliary flow from nasal passages carries material both forward, out of the nares, and backwards into the oropharynx.

Serum antibody titers against both serotype 1 and serotype 6 increased substantially in three of the calves fed leukotoxin mutants. Since the calves were killed on day 10, little time was available for an immune response in the 7 calves which did not colonize until day 6 or 7. It is therefore likely that feeding the organism elicited or at least facilitated an immune response prior to the detected nasal colonization.

Both serotypes 1 and 6 were recovered from nasal mucus in high amounts from every calf, most often as a mixed infection with both serotypes. In two cases, by day 10 serotype 1 had outgrown serotype 6 to become the predominant flora. In one case, serotype 6 became the predominant flora. These results suggest that serotype 6 is nearly equal in its ability to colonize under the chosen conditions. Given observations that serotype 6 strain NADC D174 elicits severe pneumonia in calves after intratracheal inoculation, one would expect that respiratory disease would occur in calves under conditions in the field. In fact, serotype 6 *P. haemolytica* has been recovered previously from nasal passages of calves in field trials and from lungs of calves which succumbed to pneumonic pasteurellosis. While serotype 1 remains the most common isolate in both nasal passages of stressed calves and from pneumonic lung, serotype 6 makes up a significant percentage of *P. haemoytica* isolations from nasal mucus or lung (about 10%) under these conditions.

Thus, in-frame leukotoxin deletion mutants of *P. haemolytica* are capable of colonizing the nasopharynx of calves made susceptible with concurrent IBR virus infection. Such infection was not sufficient to prevent colonization by wild-type *P. haemolytica*. Feeding the leukotoxin mutants to calves concurrently with IBR virus exposure allowed one calf to become colonized to a high level in its nasal passages and appeared to result in seroconversion to *P. haemolytica* in 3 of 4 calves. Both *P. haemolytica* serotypes 1 and 6 are capable of explosive colonization during respiratory virus infection, and each can do so in the presence of the other.

TABLE 1

IHA antibody titers against *Pasteurella haemolytica* serotypes 5 and 6 and leukotoxin neutralization titers before and after vaccination. First dose of vaccine on day 0, 2$^{nd}$ dose on day 21. All animals intratracheally challenged with wild-type serotypes 5 and 6 on day 28. n = 5 per group.

|  |  | Day 0 | Day 14 | Day 28 | Day 33 |
|---|---|---|---|---|---|
| Serotype 5 | Vaccinate | 2.4 | 6.0 | 6.2 | 6.8 |
|  | Control | 1.2 | 1.8 | 2.6 | 8* |

TABLE 1-continued

IHA antibody titers against *Pasteurella haemolytica* serotypes 5 and 6 and leukotoxin neutralization titers before and after vaccination. First dose of vaccine on day 0, 2$^{nd}$ dose on day 21. All animals intratracheally challenged with wild-type serotypes 5 and 6 on day 28. n = 5 per group.

|  |  | Day 0 | Day 14 | Day 28 | Day 33 |
|---|---|---|---|---|---|
| Serotype 6 | Vaccinate | 1.4 | 6.2 | 6.2 | 6.8 |
|  | Control | 0.8 | 1.4 | 1.4 | 6* |
| Leukotoxin** | Vaccinate | 0.4 | 3.0 | 3.4 | — |

*One surviving sheep, 4 animals died 2 days after challenge and were not tested.
**Control animals were not tested

TABLE 2

Lung lesion scores and postmortem lung bacterial culture results 5 days after intratracheal challenge with *Pasteurella haemolytica* serotypes 5 and 6. (n = 5 for each group, numbers expressed ± 95% confidence interval)

|  | Percent lung lesions** | Geometric mean *P. haemolytica* in lung |
|---|---|---|
| Vaccinates | 3.5 ± 2.8* | $1.2 \times 10^1 \pm 0.9 \times 10^{1*}$ |
| Controls | 52.1 ± 21.7 | $6.3 \times 10^7 \pm 2.5 \times 10^1$ |

*Significantly different from control values, p < 0.001
**Percentage involvement of each lobe estimated and multiplied by the lobes' contribution to overall air exchange.

TABLE 3

IHA antibody titers against *Pasteurella haemolytica* serotype 1 and leukotoxin neutralization titers before and after vaccination. First dose of vaccine on day 0, 2$^{nd}$ dose on day 21. All animals intratracheally challenged with wild-type serotype 1 on day 28. (n = 6 for controls and 5 each for vaccinated groups)

|  |  | Day −3 | Day 21 | Day 28 | Day 32 or 33 |
|---|---|---|---|---|---|
| IHA titer | IM vaccinate | 2.6 | 3.4 | 4.8 | 5.8 |
|  | Oral vaccinate | 3.0 | 7.6 | 7.0 | 7.6 |
|  | Control | 2.2 | 3.3 | 3.5 | 5.8* |
| Leukotoxin** | IM vaccinate | 6.8 | 6.8 | 7.4 | 7.8 |
|  | Oral vaccinate | 6.6 | 7.8 | 7.4 | 8.0 |
|  | Control | 6.8 | 6.3 | 6.2 | 6.8* |

*Four surviving calves, 2 animals died 3 days after challenge and were not tested.

TABLE 4

Lung lesion scores and postmortem lung bacterial culture results 4 or 5 days after intratracheal challenge with *Pasteurella haemolytica* serotype 1. (n = 6 for controls and 5 each for vaccinated groups, numbers expressed ± 95% confidence interval)

|  | Percent lung lesions*** | Geometric mean *P. haemolytica* in lung |
|---|---|---|
| IM vaccinate | 7.0 ± 7.3* | $1.8 \times 10^2 \pm 0.7 \times 10^{2*}$ |
| Oral vaccinate | 4.4 ± 4.5** | $1.4 \times 10^2 \pm 0.6 \times 10^{2*}$ |
| Controls | 32.0 ± 13.4 | $1.6 \times 10^6 \pm 1.0 \times 10^2$ |

*Significantly different from control values, p < 0.01
**Significantly different from control values, p < 0.02
***Percentage involvement of each lobe estimated and multiplied by the lobes' contribution to overall air exchange.

TABLE 5

Shedding of *P. haemolytica* in nasal mucus of calves infected with IBR virus on day 0.

| Calf* | Phenotype** | Day 6 CFU/ml | Day 6 % St-1† | Day 6 CFU/ml | Day 6 % St-1 | Day 10 CFU/ml | Day 10 % St-1 |
|---|---|---|---|---|---|---|---|
| 15 | mutant | $4.0 \times 10^7$ | >95 | $4.0 \times 10^6$ | 50 | $1.0 \times 10^8$ | >95 |
|  | wild-type | none | — | $1.5 \times 10^8$ | >95 | $2.0 \times 10^8$ | 80 |
| 19 | mutant | $5.6 \times 10^7$ | 85 | $1.1 \times 10^7$ | 65 | none | — |
|  | wild-type | none | — | $1.1 \times 10^8$ | 10 | $5.0 \times 10^8$ | <5 |
| 28 | mutant | $4.3 \times 10^7$ | 80 | $2.5 \times 10^7$ | 70 | $1.2 \times 10^7$ | 60 |
|  | wild-type | none | — | $1.2 \times 10^8$ | 55 | $1.9 \times 10^8$ | 20 |
| 29 | mutant | $1.6 \times 10^7$ | >95 | $2.0 \times 10^6$ | >95 | $4.0 \times 10^6$ | >95 |
|  | wild-type | none | — | $6.0 \times 10^7$ | 15 | $1.3 \times 10^8$ | >95 |
| 5 | wild-type | none | — | $2.0 \times 10^8$ | 60 | $1.5 \times 10^8$ | 60 |
| 17 | wild-type | none | — | $1.5 \times 10^8$ | 50 | $4.1 \times 10^7$ | 40 |
| 18 | wild-type | none | — | $2.0 \times 10^8$ | 10 | $2.0 \times 10^8$ | >95 |
| 30 | wild-type | none | — | $2.8 \times 10^8$ | 30 | $6.0 \times 10^8$ | 30 |

*Calves 15, 19, 28, and 29 exposed to serotype 5 and 6 P. haemolytica leukotoxin mutants intranasally on day 5. All calves exposed to wild-type P. haemolytica serotype 5 and 6 on day 6.
**Leukotoxin mutants are non-hemolytic; wild-type displays β-hemolysis.
†20 representative colonies serotyped, when available.

REFERENCES

1. Briggs R. E., Tatum F. M., Casey T. A., Frank G. H. Characterization of a restriction endonuclease, PhaI, from *Pasteurella haemolytica* serotype A1 and protection of heterologous DNA by a cloned PhaI methyltransferase gene. Appl. Environ. Microbiol. 60:2006–2010. 1994.

2. Thomas C. M. Plasmid replication. In: PLASMIDS: A PRACTICAL APPROACH. K. G. Hardy, ed. IRL Press Limited, Oxford, England. 1987.

3. Tatum F. M., Briggs R. E., Sreevatsan S. S., Zehr E. S., Ling Hsuan S., Whiteley L. O., Ames T. R., Maheswaran S. K. Construction of an isogenic leukotoxin deletion mutant of *Pasteurella haemolytica* serotype 1: characterization and virulence. Microb. Pathog. 24: 37–46, 1998.

4. Conrad M., Topal M. D. Modified DNA fragments activate NaeI cleavage of refractory DNA sites. Nucleic Acids Res; 20:5127–5130. 1992.

5. Murphy G. L., Whitworth L. C., Clinkenbeard K. D., Clinkenbeard P. A. Hemolytic activity of the *Pasteurella haemolytica* leukotoxin. Infect. Immun. 63:3209–3212. 1995.

6. Fedorova N. D., Highlander S K. Generation of targeted nonpolar gene insertions and operon fusions in *Pasteurella haemolytica* and creation of a strain that produces and secretes inactive leukotoxin. Infect. Immun. 65:2593–2598. 1997.

7. Briggs R. E., Frank G. H., Zehr E. S. Development and testing of a selectable challenge strain of *Pasteurella haemolytica* for studies of upper-respiratory colonization of cattle. Am. J. Vet. Res. 59: 401–405, 1998.

8. Frank G. H., Smith P. C. Prevalence of *Pasteurella haemolytica* in transported calves. Am. J. Vet. Res. 44:981–985. 1983.

9. Frank G. H., Wessman G. E. Rapid plate agglutination procedure for serotyping *Pasteurella haemolytica*. J. Clin. Microbiol. 7:142–145. 1978.

10. Frank G. H., Briggs R. E., Loan R. L., Purdy C. W., Zehr E. S. Serotype-specific inhibition of colonization of the tonsils and nasopharynx of calves by *Pasteurella haemolytica* serotype A1 after vaccination with the organism. Am. J. Vet. Res. 55: 1107–1110. 1994.

11. Frank G. H., Briggs R. E., Zehr E. S. Colonization of the tonsils and nasopharynx of calves by a rifampicin-resistant *Pasteurella haemolytica* and its' inhibition by vaccination. Am. J. Vet. Res. 56: 866–869. 1995.

12. Frank G. H., Briggs R E., Loan R. W., Purdy C. W., Zehr E. S. Respiratory tract disease and mucosal colonization by *Pasteurella haemolytica* in transported cattle. Am. J. Vet. Res. 57: 1317–1320. 1996.

13. Purdy C. W., Cooley J. D., Straus D. C. Cross-protection studies with three serotypes of *Pasteurella haemolytica* in the goat model. Curr. Microbiol. 36: 207–211. 1998.

14. McVey D. S., Loan R. W., Purdy C. W., Richards A. E. Antibodies to *Pasteurella haemolytica* somatic antigens in two models of the bovine respiratory disease complex. Am. J. Vet. Res. 50:443–447. 1989.

15. Jones G. E., Donachie D. W., Sutherland A. D., Knox D. P., Gilmour J. S. Protection of lambs against experimental pneumonic pasteurellosis by transfer of immune serum. Vet. Microbiol. 20:59–71. 1989.

16. Schimmel D., Erler W., Diller R. [The significance of antibodies to *Pasteurella haemolytica* A1 in the colostrum of cows and blood serum of calves]. Berl Munch Tierarztl Wochenschr 105:87–89. 1992.

17. Frank G. H., Briggs R. E. Colonization of the tonsils of calves with *Pasteurella haemolytica*. Am. J. Vet. Res 53:481–484. 1992.

18. Frank G. H., Briggs R. E., and Debey B. M. Bovine tonsils as reservoirs for *Pasteurella haemolytica*: Colonisation, immune response, and infection of the nasopharynx. In: Pasteurellosis in Production Animals (Workshop Proceedings, Australian Centre for International Agricultural Research.) pp 83–88. 1992.

We claim:

1. A method of inducing immunity to pneumonic pasteurellosis in ruminants, comprising the step of:
   administering to a ruminant a live P. haemolytica bacterium which contains no non-P. haemolytica DNA and which, when in a physiological environment, (a) expresses no biologically active leukotoxin and (b) expresses a mutant leukotoxin molecule which is a deletion mutant of about 66 kDa which lacks amino acids 34 to 378 of the wild-type leukotoxin and which induces antibodies which specifically bind to and neutralize biologically active leukotoxin.

2. The method of claim 1 wherein the step of administering is via the oral route.

3. The method of claim 2 wherein the bacterium is top-dressed on a feed of the ruminant.

4. The method of claim 1 wherein the step of administering comprises injecting the bacterium subcutaneously.

5. The method of claim 1 wherein the step of administering comprises injecting the bacterium intradermally.

6. The method of claim 1 wherein the step of administering comprises injecting the bacterium intramuscularly.

7. The method of claim 1 wherein the step of administering is via the nose.

8. The method of claim 1 wherein the live bacterium is lyophilized.

9. The method of claim 1 wherein the live bacterium is reconstituted from a lyophilized preparation.

10. A method of inducing immunity to pneumonic pasteurellosis in ruminants comprising, administering a vaccine formulation which comprises:
   (a) a killed P. haemolytica bacterium which contains no non-P. haemalytica DNA and which expressed a deletion mutant leukotoxin when it was alive; and
   (b) a P. haemolytica deletion mutant leukotoxin in the form of a purified protein or in a preparation selected from the group consisting of a bacterial lysate, a bacterial extract, and a culture supernatant;
   wherein the deletion leukotoxin molecules of (a) and (b) have a molecular weight of about 66 kDa, lack amino acid residues 34 to 378 of the wild-type leukotoxin molecule, and induce antibodies which specifically bind to an neutralize biologically active leukotoxin.

11. The method of claim 10 wherein the step of administering is via the oral route.

12. The method of claim 11 wherein the vaccine formulation is top-dressed on a feed of the ruminant.

13. The method of claim 10 wherein the step of administering comprises injecting the vaccine formulation subcutaneously.

14. The method of claim 10 wherein the step of administering comprises injecting the vaccine formulation intradermally.

15. The method of claim 10 wherein the step of administering comprises injecting the vaccine formulation intramuscularly.

16. The method of claim 10 wherein the step of administering is via the nose.

17. A feed for ruminants which comprises a live P. haemolytica bacterium which contains no non-P. haemolytica DNA and which, when in a physiological environment, (a) expresses no biologically active leukotoxin and (b) expresses a mutant leukotoxin molecule which is a deletion mutant of about 66 kDa which lacks amino acids 34 to 378 of the wild-type leukotoxin molecule and which induces antibodies which specifically bind to and neutralize biologically active leukotoxin.

18. The feed of claim 17 wherein the live bacterium is lyophilized.

19. The feed of claim 17 wherein the live bacterium is reconstituted from a lyophilized preparation.

20. A feed for ruminants which comprises:
   (a) a killed P. haemolytica bacterium which contains no non-P. haemolytica DNA and which expressed a deletion mutant leukotoxin when it was alive; and
   (b) a P. haemolytica deletion mutant leukotoxin in the form of a purified protein or in a preparation selected from the group consisting of a bacterial lysate, a bacterial extract, and a culture supernatant;
   wherein the deletion leukotoxin molecules of (a) and (b) have a molecular weight of about 66 kDa, lack amino acid residues 34 to 378 of the wild-type leukotoxin molecule, and induce antibodies which specifically bind to an neutralize biologically active leukotoxin.

21. A vaccine for reducing morbidity in ruminants, comprising a live P. haemolytica bacterium which contains no non-*P. haemolytica* DNA and which, when in a physiological environment, (a) expresses no biologically active leukotoxin and (b) expresses a form of leukotoxin molecule which is a deletion mutant of about 66 kDa which lacks amino acids 34 to 378 of the wild-type leukotoxin and which induces antibodies which specifically bind to and neutralize biologically active leukotoxin.

22. The vaccine of claim 21 wherein the live bacterium is lyophilized.

23. The vaccine of claim 21 wherein the live bacterium is reconstituted from a lyophilized preparation.

24. A vaccine for reducing morbidity in ruminants, comprising:

(a) a killed *P. haemolytico* bacterium which contains no non-*P. haemolytica* DNA and which expressed a deletion mutant leukotoxin when it was alive; and (b) a *P. haemolytica* deletion mutant leukotoxin in the form of a purified protein or in a preparation selected from the group consisting of a bacterial lysate, a bacterial extract, and a culture supernatant;

wherein the deletion leukotoxin molecules of (a) and (b) have a molecular weight of about 66 kDa, lack amino acid residues 34 to 378 of the wild-type leukotoxin molecule, and induce antibodies which specifically bind to an neutralize biologically active leukotoxin.

* * * * *

UNITED STATES PATENT AND TRADEMARK OFFICE
CERTIFICATE OF CORRECTION

PATENT NO. : 6,936,262 B2
DATED : August 30, 2005
INVENTOR(S) : Briggs and Tatum It is certified that error appears in the above-identified patent and that said Letters Patent is hereby corrected as shown below:

<u>Title page,</u>
Item [56], References Cited, OTHER PUBLICATIONS,
"Beaumont et al." reference, replace "*al* R," with -- *alc*R --.

<u>Column 23,</u>
Line 67, replace "an" with -- and --.

Signed and Sealed this

Thirtieth Day of May, 2006

JON W. DUDAS
*Director of the United States Patent and Trademark Office*